United States Patent [19]
Borden et al.

[11] Patent Number: 5,436,465
[45] Date of Patent: Jul. 25, 1995

[54] MODULAR PARTICLE MONITOR FOR VACUUM PROCESS EQUIPMENT

[75] Inventors: Peter G. Borden, San Mateo; Hung H. Quach; Derek G. Aqui, both of San Jose, all of Calif.

[73] Assignee: High Yield Technology, Inc., Sunnyvale, Calif.

[21] Appl. No.: 60,904

[22] Filed: May 13, 1993

[51] Int. Cl.[6] .................................................. G01N 15/06
[52] U.S. Cl. .................................... 250/574; 356/338
[58] Field of Search ................. 250/573, 574; 356/338, 356/339, 341, 342, 343

[56] References Cited

U.S. PATENT DOCUMENTS 4,663,522  5/1987  Welbourn et al. ................... 356/338
4,739,177  4/1988  Borden .................................. 250/574
4,979,822  12/1990  Sommer ............................... 356/338

Primary Examiner—David C. Nelms
Attorney, Agent, or Firm—Skjerven, Morrill, MacPherson, Franklin & Friel; Edward C. Kwok

[57] ABSTRACT

An apparatus and a method provide a modular design for a particle monitor of external design used in a vacuum process equipment. In one embodiment, the key elements, i.e. laser assembly, the detection module, the beam stop and a darkened surface opposite the detection module, can be independently mounted on a pump line. The particle monitors of the present invention can be mounted on both straight sections and bends of the pump line. Each key element can be accessed independently of other key elements for repair and service.

16 Claims, 2 Drawing Sheets

MODULAR PARTICLE MONITOR FOR VACUUM PROCESS EQUIPMENT

BACKGROUND OF THE INVENTION

1. Field of the Invention

The present invention relates to particle monitors used in vacuum equipment; and, in particular, the present invention relates to modular designs of particle monitors suitable for external mounting on vacuum pump lines.

2. Discussion of the Related Art

In situ particle monitors are used in many types of vacuum processing equipment, such as those used for the manufacture of VLSI integrated circuits, to detect particle levels in such equipment. One such particle monitor is disclosed in U.S. Pat. No. 5,132,548, entitled "Large Detection Area Particle Sensor for Vacuum Applications" by P. Borden et al, filed on Sep. 14, 1990, assigned to High Yield Technology Inc., and issued on Jul. 21, 1992. The principal advantage of an in situ particle monitor is that such a particle monitor provides a real-time measurement of a particle level, so that an early warning can be provided when the particle level exceed certain preset thresholds. Such early warning is valuable to minimize product loss due to particle contamination.

An in situ particle monitor is often provided in a vacuum pump line carrying gas into or out of a process chamber of a piece of vacuum processing equipment. Many integrated circuit manufacturing processes operate at intermediate pressures, i.e. those pressures which are below atmospheric but greater than a hard vacuum. Typical intermediate pressures range from 0.1 to 2 Torr. Two examples of such processes are plasma etching and chemical vapor deposition. The intermediate pressures are great enough to support particles in the gasses flowing through a process chamber of these processes. Particles are typically generated in the process chamber and are drawn into an exhaust gas line, so that a particle sensor positioned in the exhaust gas line can detect the particles carried by the effluent gas. Detecting particles using such a particle sensor is advantageous because no modification to the process chamber is required. Further, in such a configuration, the particle sensor is removed from both the bright plasma glow and the reactive chemicals which may be present in such process chamber.

A particle monitor or sensor used in an exhaust line application usually operates by laser light scattering. In such a particle monitor, a laser beam source provides a laser beam, which is focussed to travel across a pump line. Particles passing through the laser beam scatter light to photocells mounted in the vicinity of the laser beam. The photocells provide an electrical signal whenever the presence of a particle is detected. In such a particle monitor, a beam stop opposite the laser source absorbs the light in the laser beam, so as to prevent the laser beam from reflecting from the opposite wall of the pump line and impinging on the photocells.

In the prior art, an in situ particle monitor typically belongs to one of two designs. In one design, also known as a probe design, the photocells for detecting light scattering are mounted close to the laser beam and the entire sensor is inserted into the pump line. The probe design has the advantages of compactness, simplicity and high sensitivity, because of the close proximity of the photocells to the laser beam. The other design (the "external design") mounts the laser, the detection optics, and the beam stop external to the pump line, allowing the incident laser beam, as well as the scattered light, to pass through windows provided in the pump line. The external design has the advantage of removing the sensitive components of the particle monitor from the vacuum line, and is therefore more desirable when highly corrosive process effluent gasses are present, or when the gas in the line is at a temperature higher than the temperature the components of the particle sensor can tolerate.

FIG. 1 shows a particle monitor 100 of conventional external design. All components of particle monitor 100 are mounted within a box 110 that encloses pump line 104. As shown in FIG. 1, four windows 103a-103d, which are transparent to the laser light used for particle detection, are provided on pump line 104. Within box 110 is housed laser source 101, which provides a laser beam 107. Lens assembly 102 collimates and focusses laser beam 107, which enters into pump line 104 through window 103a and emerges through window 103c to terminate at laser beam stop 108. In this design, particles carried in the pump line scatter light when passing through laser beam 107. Some of the scattered light emerges from pump line 104 through window 103b. Lens 105 focusses the scattered light onto photocell 106. In FIG. 1, a black surface or mirror 109 is positioned behind window 103d on the opposite side of window 103b. Black surface or mirror 109 minimizes pick-up of stray light from the wall of pipe line 104. If not minimized, such stray light can be collected by lens 105, causing noise in photocell 108.

However, the external design suffers the disadvantage of bulk. This is because, in an external design particle sensor, the components are built around the pump line in a connected structure, so as to provide support to the particle sensor. For example, particle sensor 100, which is sensitive to vibration, is firmly held in place by box 110. However, box 110 requires considerable space, thereby limiting the choices of locations at which particle sensor 100 can be installed. Also, customizing of particle sensor 100 for various application may require box 110 be redesigned for each application. Such customization may be required to fit particle sensor 100 into certain spaces, or to accommodate difference sizes or shapes of pump line 104. Unfortunately, in many applications, little space is available at the optimal mounting location for particle detection, which is usually very near the process chamber, at or before any bend in the pump line. In many instances, the particle sensor has to be mounted further away, where it is less efficient. In some instances, such a particle monitor simply cannot be installed.

SUMMARY OF THE INVENTION

In accordance with the present invention, a structure and a method provide a modular particle monitor for particle detection in a vacuum process equipment. The particle sensor of the present invention comprises separately mounted key elements, including a laser source, a detector module, a beam stop and a darkened surface to minimize stray light from a back wall of the vacuum line.

Because the key elements in the particle monitors of the present invention can be individually adjusted, such particle monitors can be mounted on both straight sections and bends of the vacuum line. Each key element of the particle monitor can be independently serviced.

Because each key element of the particle monitor of the present invention is secured separately to the vacuum line, each element of a particle monitor of the present invention is simply affixed to the vacuum line by a flange connection. Such a flange connection can be provided by the KF type flange connection.

Since each key element of the particle monitor of the present invention is positioned and installed separately, customization of the particle monitor to a given piece of vacuum equipment, especially where the space available for installing a particle monitor is limited, is greatly simplified.

The modular design provides flexibility to configure a particle monitor for use in diverse applications. In one embodiment, only the size of the pick-up lens in the detection module of the particle sensor need be increased to achieve high performance when mounted on a larger size vacuum line.

DESCRIPTION OF THE PREFERRED EMBODIMENTS

Unlike the particle sensors of external design in the prior art, a connected structure (e.g. box 110 of FIG. 1) enclosing all components of the particle sensor is not required in the particle sensors of the present invention. One embodiment of the present invention is illustrated by the particle sensor 200 of FIG. 2.

Figure 2:
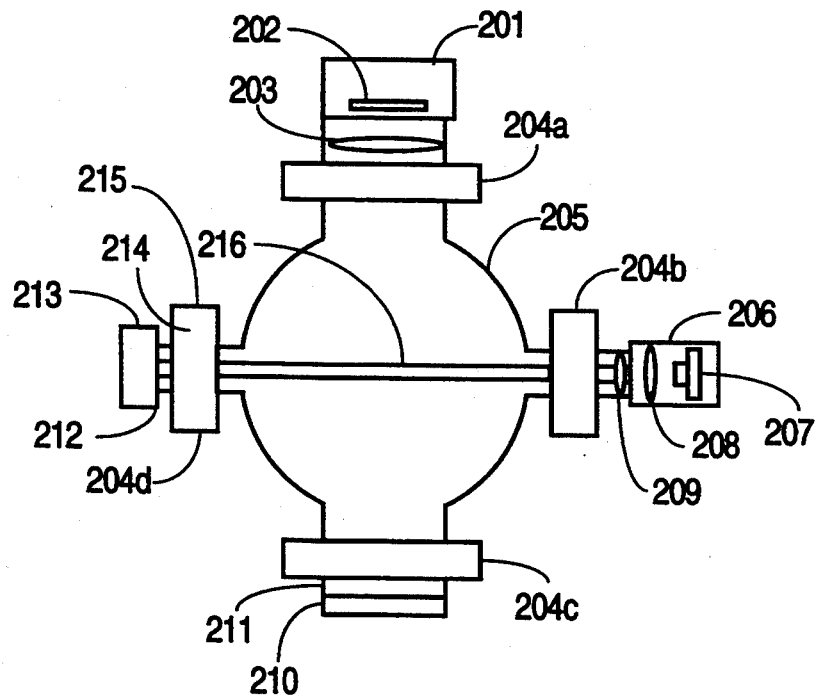
FIG. 2 shows a particle sensor 200 mounted external on pump line 205, in accordance with the present invention.

As shown in FIG. 2, the "key elements" of the particle sensor 200, including laser assembly 206, detection system 201, beam stop 213 and darkened surface 211 for minimizing stray light are each independently affixed to vacuum flanges 204a–204d. Vacuum flanges 204a–204d can be welded to a pump line 205. Thus, each key element can be positioned independently. As a result of the independent positioning, particle sensor 200 can be made to occupy less space than a particle sensor of the prior art. Further, repair and service of particle sensor 200 can be performed on each key element independently. For example, each key element, rather than the entire sensor, can be independently replaced.

Each key element is affixed to pump line 205 using KF ("Kwik-Flange TM") type flanges 204a–204d of the appropriate size. One commonly used size is 25 mm. KF type flanges are standard vacuum flanges available from a number of sources, such as MDC, Hayward, Calif. Each KF type flange connection has two flanges held together by a clamp, with an O-ring held in place between the flanges. The clamp can be quickly removed, thereby allowing straightforward removal, replacement or cleaning of the components affixed to the flanges.

Laser assembly 206 comprises laser source 207, which can be implemented by laser model 301 available from Sony Corporation, Tokyo, Japan. Laser source 207 provides a laser beam 216, which is collimated by lens 208 and focussed by a cylindrical lens 209 of a 100 mm focal length. In this embodiment, lens 208 is an OPL lens available from NSG Corporation, Tokyo, Japan. Cylindrical lens 209 can be obtained from Melles Griot of Irvine, Calif. Laser beam 216 travels across pump line 205 to terminate at the beam stop module 213, which includes a darkened block 212 to absorb laser beam 216.

Detection system 201 and darkened surface 211 are held in place with KF flanges of appropriate size, such as 50 mm. Detection system 201 comprises lens 203 ("pick-up lens") of a suitable focal length to gather the scattered light onto photodetector 202. Lens 203 is available from the aforementioned Melles Griot, and photodetector 202 can be implemented by a PIN photodiode made by Hamamatsu Corporation, Hamamatsu, Japan. The darkened surface 211 is provided by a black anodized cup 210. Darkened surface 211 provides a dark surface to minimizing the amount of stray light focussed onto the photodetector.

Figure 3:
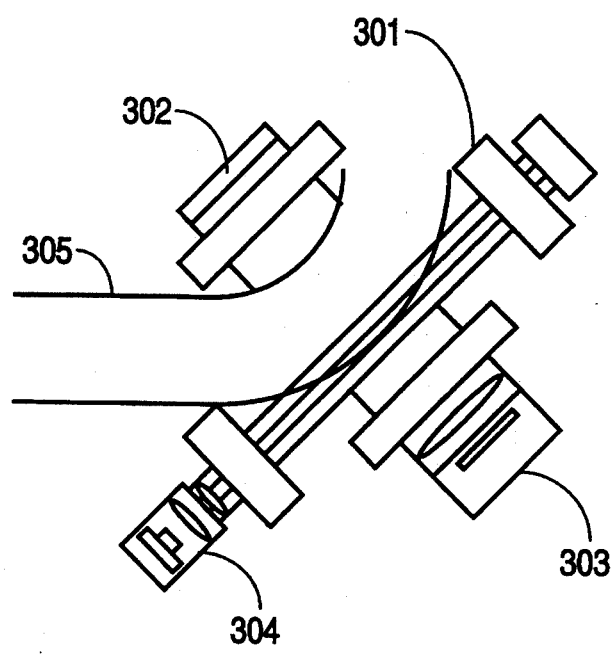
FIG. 3 shows a particle sensor 300 of the present invention mounted on a bend in a pump line 305.

A particle sensor of the present invention need not be installed on a straight section of the pump line. In fact, FIG. 3 shows a particle sensor 300 installed at a bend of a pump line. Because each key element of particle sensor 300 is mounted independently, many configurations are possible.

As shown in FIG. 3, laser assembly 304, beam stop 301, detection system 303 and darkened surfaces 302 are independently mounted on a bend in pipeline 305. The components of laser assembly 305, beam stop 301, detection system 303 and darkened surface 302 are the same as those of laser assembly 206, beam stop 213, detection system 201 and darkened surface 211 of FIG. 2, respectively. In particle sensor 300, all key elements are mounted in the same plane in the bend of pipeline 305.

Figure 1:
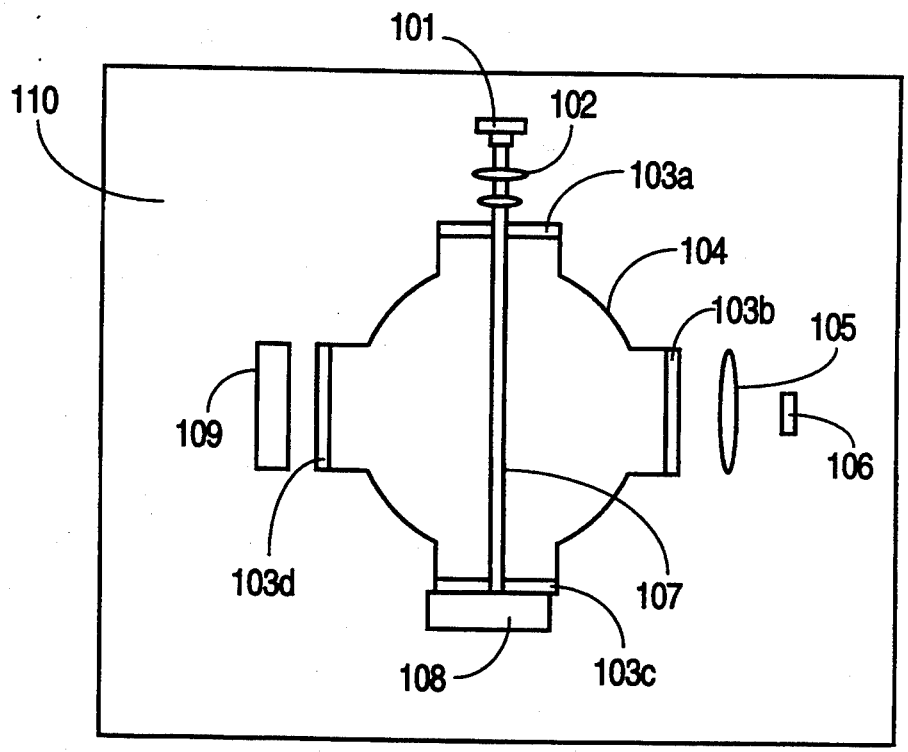
FIG. 1 shows a particle sensor 100 of the conventional external design.

Particle sensor 300 illustrates the advantage of a modular external design particle sensor of the present invention over the conventional external design which required a containment, such as box 110 of FIG. 1. In the modular design of the present invention, such as illustrated by FIG. 3, the bend in the pipeline can be accommodated without modification to the sensor design. With a conventional design of box 110, for example, extensive modification would be required. The ability to install a particle sensor at the bend of a pump line is of particular importance in certain applications, since particles settle out of a low pressure gas flow when the gas flows through a bend in the pump line. Thus, monitoring particle levels at a bend of the pump line provides more accurate measurement of the particle level than monitoring the particle level from a position downstream of the bend. The benefits provided by the present invention are particular noteworthy, considering that, in certain kinds of vacuum process equipment, it is typical to include a bend in the pump line a short distance away from the process chamber.

The above detailed description is provided to illustrate the specific embodiments of the present invention and is not intended to be limiting. Numerous variations and modifications are possible within the scope of the present invention. For example, particle sensors of the present invention can be installed without modification in pump lines of any practical sizes, including the typical 25, 40, 50, 80 or 100 mm pump lines. For the larger pump lines, increasing correspondingly the size of the pick-up lens allows more scattered light to be collected, thereby providing a simple way to achieve higher performance in the particle sensor. It is noteworthy that, even with a larger pick-up lens in the detector module, the laser assembly and the beam stop modules of the particle sensor need not be made correspondingly larger. The present invention is defined by the following claims.

We claim:

1. A particle monitor for mounting on a vacuum line, wherein a gas flowing through said vacuum line carries particles to be detected, comprising:
   a laser source for providing a laser beam to be projected across said vacuum line;
   a beam stop positioned to absorbing said laser beam; and
   a detection module positioned to detect light scattered by said particles as they are carried by said gas flow through said laser beam;
   wherein said detection module is mounted on said vacuum line separately from both said laser source and said beam stop.

2. A particle detector as in claim 1, further comprising a darkened surface mounted on said vacuum line and positioned opposite said detection module to minimize stray light in said vacuum line.

3. A particle detector as in claim 1, wherein said particle detector is mounted on a bend in said vacuum line.

4. A particle detector as in claim 1, wherein said detection module comprises a pick-up lens having a size which is commensurate with the size of said vacuum line.

5. A method for mounting a particle monitor on a vacuum line, wherein a gas flowing through said vacuum line carries particles to be detected, comprising:
   mounting on said vacuum line a laser source for providing a laser beam to be projected across said vacuum line;
   mounting on said vacuum line a beam stop positioned to absorb said laser beam; and
   mounting on said vacuum line a detection module positioned to detect scattered light as said particles carried by said gas flow through said laser beam;
   wherein said detection module is mounted on said vacuum line separately from both said laser source and said beam stop.

6. A method as in claim 5, further comprising the step of mounting a darkened surface on said vacuum line at a position opposite said detection module to minimize stray light in said vacuum line.

7. A method as in claim 5, wherein said mounting steps are performed on a bend in said vacuum line.

8. A method as in claim 5, wherein said step of mounting on said vacuum line a detection module comprises the step of providing a pick-up lens having a size which is commensurate with the size of said vacuum line.

9. A particle monitor for mounting on a vacuum line, wherein a gas flowing through said vacuum line carries particles to be detected, comprising:
   a laser source for providing a laser beam to be projected across said pump vacuum line;
   a beam stop positioned to absorb said laser beam; and
   a detection module positioned to detect light scattered by said particles as they are carried by said gas flow through said laser beam;
   wherein at least one-of said laser source, said beam stop, and said detection module is separately mounted on said vacuum line using a KF type flange connection.

10. A particle detector as in claim 9, further comprising a darkened surface mounted on said vacuum line and positioned opposite said detection module to minimize stray light in said vacuum line.

11. A particle detector as in claim 9, wherein said particle detector is mounted on a bend in said vacuum line.

12. A particle detector as in claim 9, wherein said detection module comprises a pick-up lens having a size which is commensurate with the size of said vacuum line.

13. A method for mounting a particle monitor on a vacuum line, wherein a gas flowing through said vacuum line carries particles to be detected, comprising:
   mounting on said vacuum line a laser source for providing a laser beam to be projected across said vacuum line;
   mounting on said vacuum line a beam stop positioned to absorb said laser beam; and
   mounting on said vacuum line a detection module positioned to detect scattered light as said particles carried by said gas flow through said laser beam;
   wherein at least one of said laser source, said beam stop, and said detection module is separately mounted on said vacuum line using a KF type flange connection.

14. A method as in claim 13, further comprising the step of mounting a darkened surface on said vacuum line at a position opposite said detection module to minimize stray light in said vacuum line.

15. A method as in claim 13, wherein said mounting steps are performed on a bend in said vacuum line.

16. A method as in claim 13, wherein said step of mounting on said vacuum line a detection module comprises the step of providing a pick-up lens having a size which is commensurate with the size of said vacuum line.

* * * * *